(12) United States Patent
Khalili

(10) Patent No.: US 7,524,325 B2
(45) Date of Patent: Apr. 28, 2009

(54) FASTENER RETENTION SYSTEM

(76) Inventor: Farid Bruce Khalili, 5 Carlton Ave., Briar Cliff Manor, NY (US) 10510

( * ) Notice: Subject to any disclaimer, the term of this patent is extended or adjusted under 35 U.S.C. 154(b) by 325 days.

(21) Appl. No.: 10/693,699

(22) Filed: Oct. 27, 2003

(65) Prior Publication Data

US 2004/0087951 A1     May 6, 2004

Related U.S. Application Data

(60) Provisional application No. 60/422,978, filed on Nov. 4, 2002, provisional application No. 60/479,797, filed on Jun. 20, 2003, provisional application No. 60/476,642, filed on Jun. 9, 2003.

(51) Int. Cl.
*A61B 17/80* (2006.01)
(52) U.S. Cl. ..................................... 606/290
(58) Field of Classification Search ............. 606/69–71, 606/72–73, 280, 281, 286, 288, 289–291, 606/296, 300, 305, 316, 294–295, 298
See application file for complete search history.

(56) References Cited

U.S. PATENT DOCUMENTS

| | | | | |
|---|---|---|---|---|
| 4,484,570 A * | 11/1984 | Sutter et al. | ........... | 606/72 |
| 5,261,910 A * | 11/1993 | Warden et al. | ........... | 606/61 |
| 5,578,034 A * | 11/1996 | Estes | ........... | 606/61 |
| 5,643,265 A * | 7/1997 | Errico et al. | ........... | 606/70 |
| 5,725,580 A * | 3/1998 | Cloutier et al. | ........... | 623/16.11 |
| 5,735,853 A * | 4/1998 | Olerud | ........... | 606/71 |
| 5,954,722 A * | 9/1999 | Bono | ........... | 606/61 |
| 6,261,291 B1 * | 7/2001 | Talaber et al. | ........... | 606/69 |
| 6,302,883 B1 * | 10/2001 | Bono | ........... | 606/69 |
| 6,306,136 B1 * | 10/2001 | Baccelli | ........... | 606/61 |
| 7,001,359 B2 * | 2/2006 | Rogers | ........... | 604/118 |
| 2003/0078583 A1 * | 4/2003 | Biedermann et al. | ........... | 606/69 |
| 2003/0149434 A1 * | 8/2003 | Paul | ........... | 606/71 |
| 2004/0092938 A1 * | 5/2004 | Carli | ........... | 606/73 |

* cited by examiner

*Primary Examiner*—Eduardo C Robert
*Assistant Examiner*—James L Swiger, III
(74) *Attorney, Agent, or Firm*—Standley Law Group LLP

(57) ABSTRACT

A vertebral plate system and associated method minimizes the number of required multiple configurations and sizes of hardware on hand during surgery for repair, stabilization or fusion of bone segments. A novel aspect of the invention is a resilient split ring that cooperates with angled contact surfaces in a plate for allowing convenient and fast dynamic locking between the plate and a bone screw. In another aspect of the present invention, a screw or similarly elongated fastener having a generally spherical or part-spherical head with a section of helical threads is configured in a generally horizontal band and positioned around a maximum-diameter section of the head. The screw is loosely retained to a first structure by a snap-ring formed from a ring of elastic material having a slot cut so that the ring is a "C" ring. The ring is seated on an annular shoulder formed in a through-hole in the first structure. The section of the through-hole above the shoulder tapers inwardly in an upward direction to a minimum diameter that is smaller than the outside diameter of the ring when the ring is in an unstressed state. The inner diameter of the ring has an edge that is adapted to cooperate with and ride in the threads on the screw head.

6 Claims, 10 Drawing Sheets

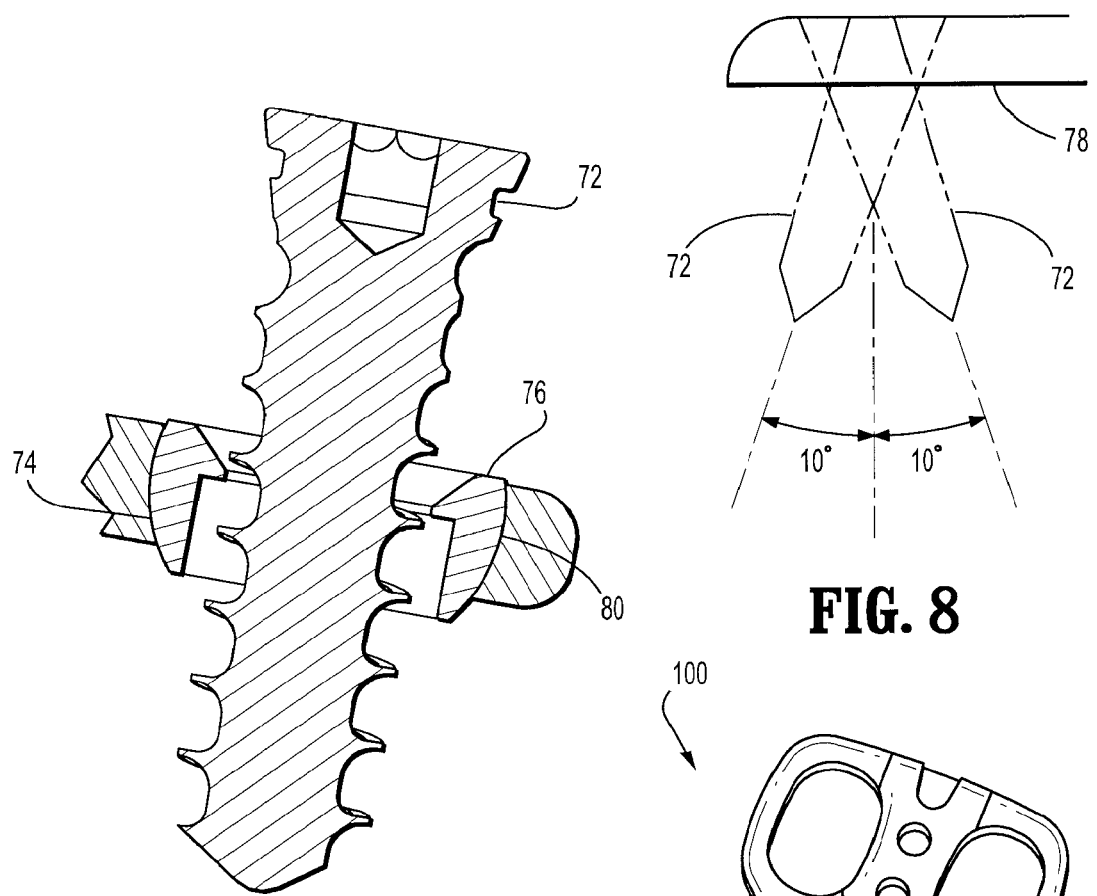
FIG. 7
FIG. 8
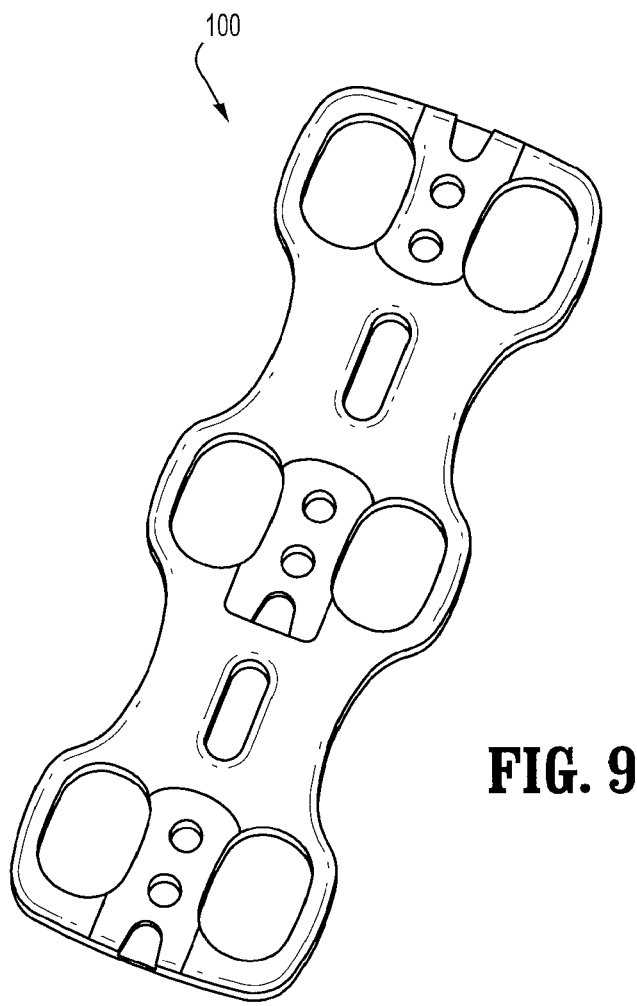
FIG. 9

FASTENER RETENTION SYSTEM

RELATED APPLICATIONS

This application is related to, and claims priority from, the following earlier-filed U.S. Provisional Patent Applications: (Serial Nos.) 60/422,978 (filed 04 Nov. 2002); 60/479,797 (filed 20 Jun. 2003); and 60/476,642 (filed 09 Jun 2003). Each is incorporated herein by reference.

TECHNICAL FIELD

The present invention relates to orthopedic implantable devices, related systems, and associated methods of use and, more particularly, to a plate system and associated method for joining two or more bone segments, such as vertebrae.

BACKGROUND OF THE INVENTION

In orthopedics it is known to use various types of plates fastened to one or more bone segments in order to join said bone segments in a predetermined relationship for stabilization and/or controlled movement. Such stabilization or controlled movement is desirable when repairing bone segments that have become deteriorated, damaged or degenerative, such as due to trauma or disease. Such stabilization or controlled movement may be used in cooperation with one or more fusion or stabilizing devices, or may be used alone.

The use of such plates or systems is employed in the treatment of vertebral bodies. It is known, for example, to use plating systems to joint one or more adjacent vertebrae for stabilization or to enhance fusion.

Various known plates used in the above-described manner are known to have shortcomings. Such shortcomings include lack of versatility so as to require multiple configurations and sizes of hardware on hand during surgery; lack of anatomical correspondence with resultant poor fit, high stress concentrations and unnatural load forces on adjacent or fused bone segments; susceptibility to pulling out due to limited arrangement of bone fastener or bone screw angles; and other shortcomings inherent to known designs.

OBJECTS AND SUMMARY OF THE INVENTION

It is an object of the present invention to provide a plate system and associated method that minimizes the number of required multiple configurations and sides of hardware on hand during surgery for repair, stabilization or fusion of bone segments.

It is an object of the present invention to provide a plate system that allows versatility and post-installation adjustment between fully dynamized, angularly adjustable and fixed bone screws.

It is an object of the present invention to provide a plate system and associated method that have optimal anatomical correspondence with bone segments to be joined to optimize fit and to minimize undesirable stress concentrations and unnatural load forces on adjacent or fused bone segments.

It is an object of the present invention to provide a plate system and associated method that minimizes susceptibility to pulling out due to limited arrangement of bone fastener or bone screw angles.

It is an object of the present invention to provide a fastener retention assembly that loosely retains a fastener with respect to one structure in a manner such that, when placed into engagement with another structure, the fastener can be easily, reliably and precisely driven into the second structure.

It is an object of the present invention to provide a fastener retention assembly that is superior to know fastener retention assemblies in applications where limitations or constraints in terms of space, precision requirements, durability, material compatibility, ease of use, safety, and other factors exist.

It is an object of the present invention to provide a fastener retention assembly that is suitable for superior performance in applications specifically directed to joining an orthopedic implant to a bone.

It is an object of the present invention to provide a fastener retention assembly that is suitable for superior performance in applications specifically directed to retaining a bone screw to a cervical plate before, during and after the bone screw is driven into a bone to which the plate is fastened.

These and other objects are described below or inherent with respect to the present invention.

A vertebral plate system and associated method according to a preferred embodiment of the present invention minimizes the number of required multiple configurations and sizes of hardware on hand during surgery for repair, stabilization or fusion of bone segments. A novel aspect of the invention is a resilient split ring that cooperates with angled contact surfaces in a plate for allowing convenient and fast dynamic locking between the plate and a bone screw.

In another aspect of the present invention, the present invention is directed to a screw or similarly elongated fastener having a generally spherical or part-spherical head with a section of helical threads being configured in a generally horizontal band and positioned around a maximum-diameter section of the head. The screw is loosely retained to a first structure by a snap-ring formed from a ring of elastic material having a slot cut so that the ring is a "C" ring. The ring is seated on an annular shoulder formed in a through-hole in the first structure. The section of the through-hole above the shoulder tapers inwardly in an upward direction to a minimum diameter that is smaller than the outside diameter of the ring when the ring is in an un-stressed state. The inner diameter of the ring has an edge that is adapted to cooperate with and ride in the threads on the screw head.

In operation, the ring is flexed or stressed in a manner to push it through the minimum diameter section at the top of the through hole of the first structure. After the ring passes down the through-hole it rests upon the shoulder and is expanded to its unstressed state. The shaft section of the screw is advanced through the ring and throughhole until the screw head begins to pass through the inner diameter of the ring. As the spherical shape of the screw head passes through the ring, the maximum diameter section with threads approaches the ring. The ring then gets slightly expanded as the maximum diameter section approaches the ring edge. At this point, further advancement of the screw causes the edge of the ring to engage the threads on the screw head. While the threads are engaged by the ring, advancement of the ring requires rotation in correspondence with the threads. This allows the screw to pass through the ring in a manner requiring much less axial force than if no threads existed, since the profile of the spherical head of the screw would require the ring to expand significantly more. After the maximum diameter section of the head is past the ring and further advancement of the screw past the ring continues, the screw reaches a point in which the ring is past the threaded section and is engaging the smooth, spherical portion of the screw head above the threaded band. The return force of the ring that biases it toward its un-stressed position causes the ring to slide up on the spherical head of the screw until it reaches an un-stressed condition, at which point the screw head cannot be backed out of the ring or the through-hole. This is because if the screw is merely pushed upward, the ring will be pushed up against the minimum diameter area of the tapered through hole and constrained against expansion adequate to let the screw head pass.

In order to release the screw and allow it to be removed from the ring and through-hole, a narrow instrument must be inserted to push downwardly on the ring, causing it to expand slightly around the screw head until the inside edge engages the screw thread, at which time counter-rotation will advance the screw head through and out of the ring and through-hole in a manner opposite of its insertion.

This assembly is adapted for use when joining the screw and the first structure to a second structure. For example, the screw can be a bone screw for joining a first structure, such as a cervical plate, to a second structure such as a vertebrae. In such a situation. The screw will have a threaded shaft adapted to be driven into a hole in said vertebrae.

BRIEF DESCRIPTION OF THE DRAWINGS

FIG. 7 is a front, cross-sectional view of a second embodiment bone screw fastener according to the present invention plate system.

FIG. 8 is a partial, side view of the preferred embodiment of the present invention plate system.

FIG. 9 is a perspective view of a second embodiment of the present invention plate system.

DESCRIPTION OF THE PREFERRED EMBODIMENTS

The present invention system and method may be used to join a variety of bone segments for stabilization, controlled or restricted movement, and/or fusion. The present invention is particularly well-suited for use in joining vertebral bodies and, thus, is presented for use in joining cervical vertebrae in the description of the preferred embodiment. This is not intended, however, to be limiting on the scope of the present invention.

Figure 1:
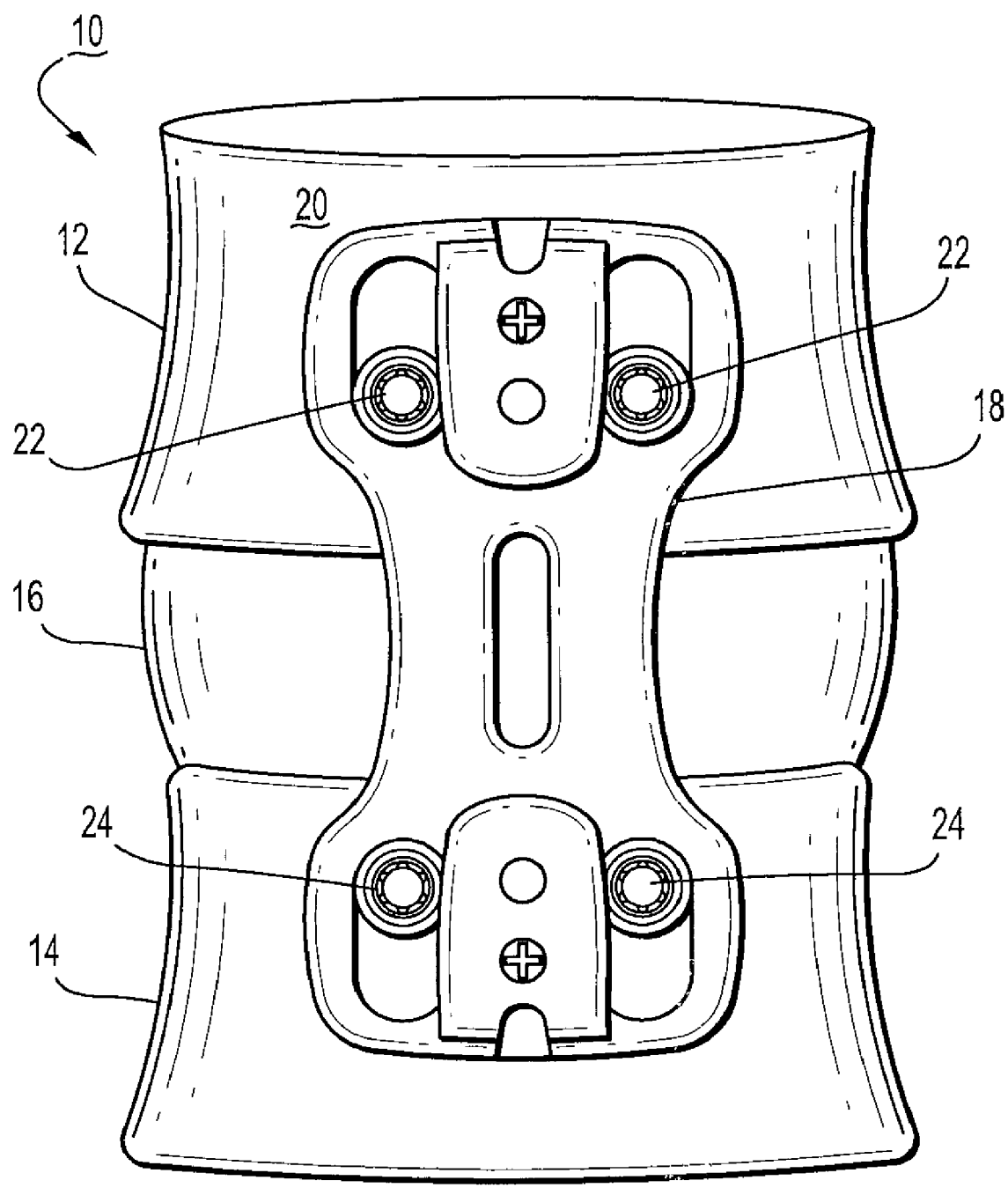
FIG. 1 is a schematic, anterior view of the preferred embodiment of the present invention plate system.

Referring to FIG. 1, there is shown schematically a group of cervical vertebral bodies (10) comprising two adjacent vertebrae (12, 14) having a disc space (16) therebetween, viewed from a side view or medial perspective. A plate (18) according to the present invention is shown fastened to the anterior side (20) of the column of vertebrae in a manner bridging across the disc space (16). Bone screws (22, 24) are used to fasten the plate in position in accordance with the present invention to stabilize the vertebrae (12, 14) for controlled movement or fusion.

Figure 2:
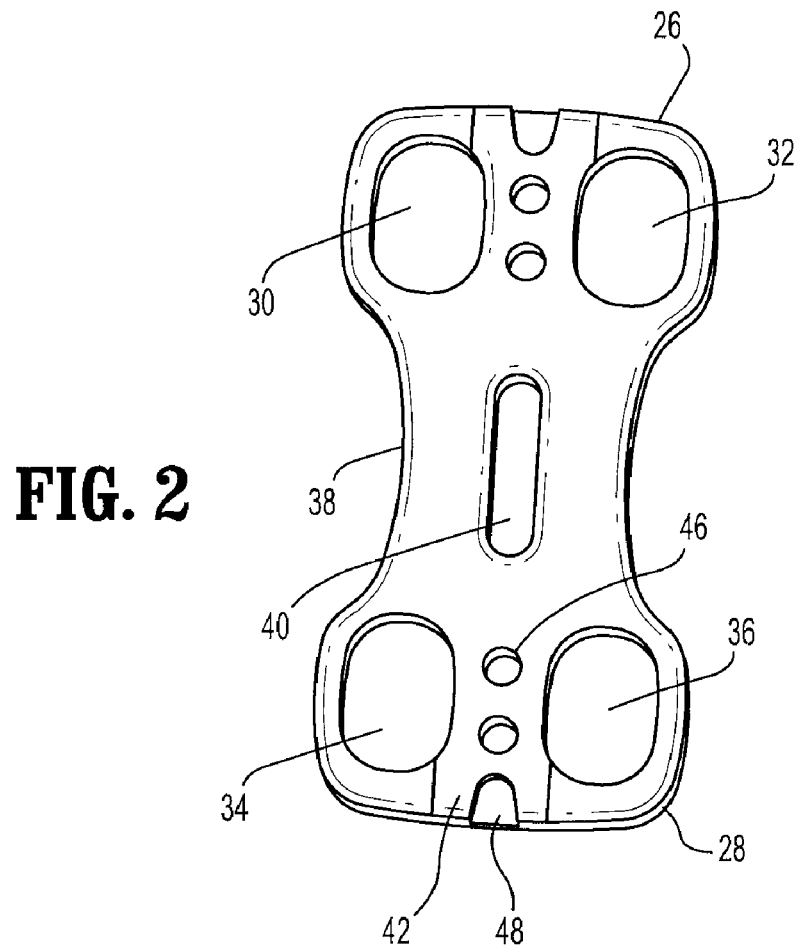
FIG. 2 is a partial, anterior view of the preferred embodiment of the present invention plate system.

The plate (18), which may be made from titanium or a suitable metal or non-metal, as shown in FIG. 2, comprises first and second ends (26,28) each having a pair of fastener slots (30, 32, 34, 36); and a middle portion (38) having a central slot (40). At the first and second ends (26,28), respectively, are a recessed area (42), a lock screw hole (44), a probe insertion hole (46), and a further recessed apex (48).

Figure 3:
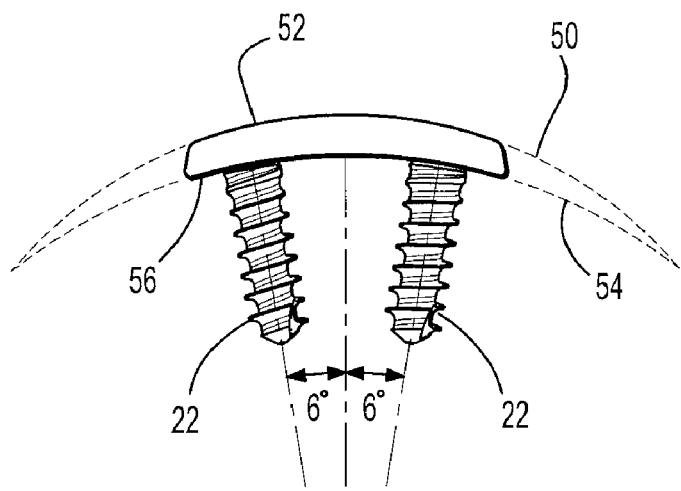
FIG. 3 is a top view of the preferred embodiment of the present invention plate system.

As shown in the top view of FIG. 3, the cross-sectional shape of the plate (18) is such that the radius (50) of the outer surface (52) is smaller than the radius (54) of the inner surface (56) which contacts the vertebrae (12, 14). This feature facilitates optimal fit and positioning of bone screws or fasteners (72) such that they are angled inward toward each other. Preferably, the, fasteners (72) are angled at about 6 degrees with respect to a direction normal to a tangent at the midpoint of the inner surface (56). This arrangement inherently reduces pullout susceptibility.

Figure 4:
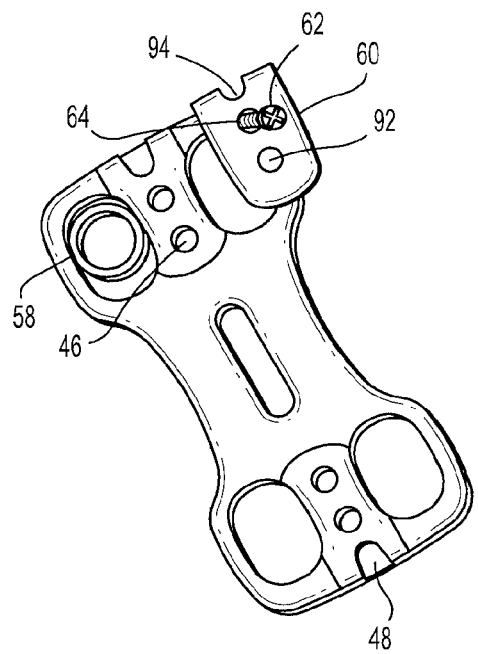
FIG. 4 is a partially exploded perspective view of the preferred embodiment of the present invention plate system.
Figure 5:
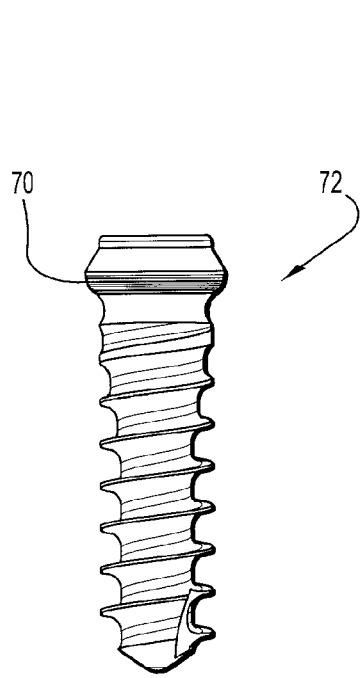
FIG. 5 is a front view of a first embodiment bone screw fastener according-to the present invention plate system.

Referring to FIG. 4, a sleeve (58) is positioned in each fastener slot (30, 32, 34, 36). Each sleeve (58) is retained in the plate (18) by a sleeve cover (60) positioned at each end (26, 28) of the plate (18). Each sleeve cover (60) fits into one of the recessed areas (42), respectively, and is fixed to the plate (18) by a lock screw (62) passing through a central hole (64) in the sleeve cover (60) which is aligned with the lock screw hole (44) for threadedly receiving the lock screw (62) therein. The profile of each sleeve cover (60) overlaps the tops of the respective sleeves (58) to prevent them from backing up and out of the plate (18). Each sleeve (58) includes a bone fastener hole (66) having threads (68) therein to retain the head (70) of a bone fastener (72) in the plate (18). Tightening each threaded head (70) causes the sleeves (58) to expand into locking engagement with the plate (18). Alternatively, as shown in FIG. 7, a snap ring (76) and cooperating channel (78) may be used in lieu of a threaded head connection.

Figure 6A:
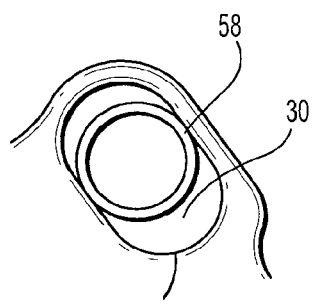
FIGS. 6(a)-6(c) are perspective views of various alternative bone screw sleeve arrangements according to the present invention.

As shown in FIG. 6(a), each sleeve (58) is round in top view and, thus, slideable within each groove (30). In addition, as shown in FIG. 7, each sleeve (58) has a semispherical lower portion (74) adapted to sit in a similarly shaped cup or seat (80) to allow relative pivoting of the sleeve (58) and fastener (72) with respect to the plate (18). Pivoting is preferably about 10 degrees from the axis, as shown in FIG. 8. This mode of enabling sliding movement and angular adjustment of the fastener (72) relative to the plate (18) is referred to as a "fully dynamized" mode. In this fully dynamized mode, the permitted sliding minimizes friction wear. In the case of fusion applications, a graft may be provided with in-line dynamic compression as the grooves (30, 32, 34, 36) are tangent to the lordotic curve of the plate (18).

Figure 6B:
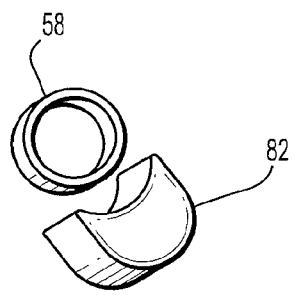

Referring to FIG. 6(b), a crescent shaped insert (82) may be positioned in one or more of the grooves (30) to constrain the sleeve (58) from translation within the groove while allowing pivoting of the sleeve (58) and fastener (72) with respect to the plate (18). The crescent insert (82) has a concave end (84) and a convex end (86). The concave end (84) forms a semispherical cup section for enabling the sleeve (58) and fastener (72) to pivot relative to the plate (18). This mode allows variable angle adjustment of the bone fastener (72) while prohibiting sliding movement.

Figure 6C:
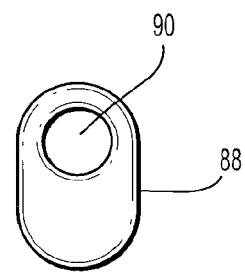

Another alternative for mounting the fastener (72) to the plate (18) is a fixed angle mode in which the bone fastener (72) neither slides nor rotates, as shown in FIG. 6(c). This is accomplished by using a modified sleeve (88) that is shaped and sized to fill the entire groove (30). The modified sleeve (88) cannot slide within the groove (30) and it has a threaded opening (90) adapted to fixedly attach the fastener (72) thereto.

Referring to FIG. 4, each sleeve cover (60) has a probe insertion hole (92) that aligns with the probe insertion hole (46) of the plate (18) when the sleeve cover (60) is positioned thereon. The two probe insertion holes (46, 92), when aligned, allow a probe or other instrument (not shown) to be positioned therein to pin or hold the plate (18) against the bone or vertebrae to which the plate (18) will be fastened during installation. Each sleeve cover (60) also includes an apex cutout (94) that, when aligned with the apex recess (48) of the plate (18), provides clearance for the esophagus of a patient in which the plate (18) is installed in the cervical region.

While the use of the sleeve covers (60) constrains each fastener (72) and sleeve (58) while allowing pivoting, as shown in FIG. 8, another significant advantage is the ability to remove the sleeve covers (60) post-installation to adjust or change to or from any one of the fasten modes of fully dynamized, variable angle, and fixed angle.

In use, the plate (18) is positioned against the vertebrae (12, 14) to be joined and held in place while a plurality of fasteners (72) are inserted through the grooves (30, 32, 34, 36) and driven into the vertebrae (12, 14). Each fastener (72) is mated with one of the sleeve (58) or modified sleeve (88). The sleeve covers (60) are fastened to the plate (18) using lock screws (62) so that the sleeve covers (60) overlap and prevent backing out by the fasteners (72).

Alternatively, as shown in FIG. 9, a plate (100) according to another embodiment of the present invention has three sets of grooves (102) adapted to receive a total of six bone fasteners (not shown) and adapted to span and connect three vertebrae. The plate (100) is similar to the above-described first embodiment in other respects.

Figure 10:
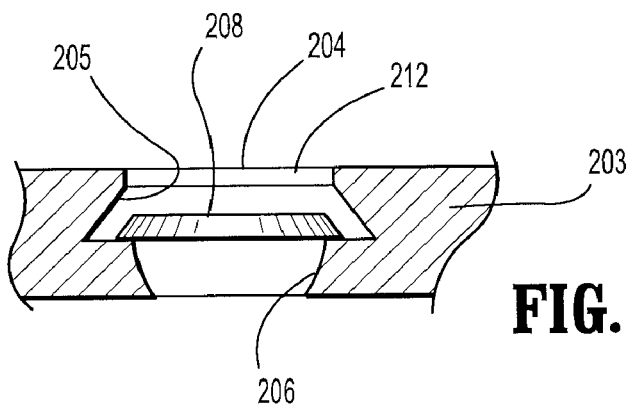
FIG. 10 is a partial, cross-sectional view of a third embodiment of the present invention plate system directed to a locking system for retaining a plate to bone structure.
Figure 11:
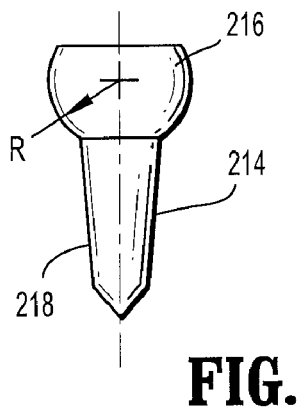
FIG. 11 is a side view of a bone screw according to the third embodiment of the present invention.
Figure 12:
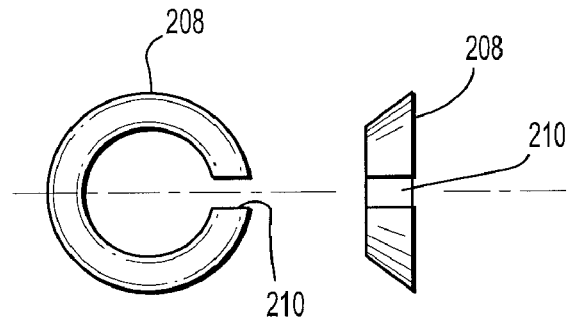
FIG. 12 is a front and side view of a locking ring according to the third embodiment of the present invention.
Figure 13:
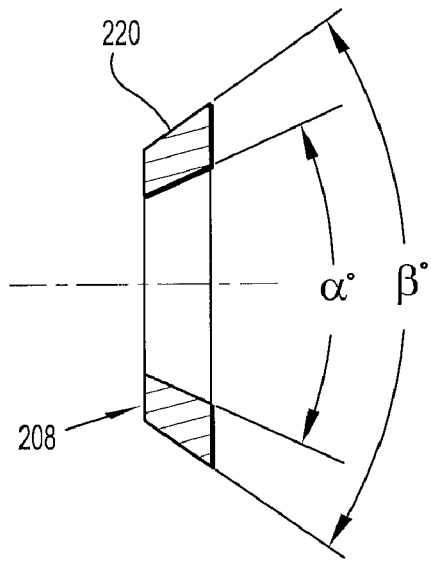
FIG. 13 is a side, cross-sectional view of the locking ring according to FIG. 12.

Another embodiment of the present invention directed to a system for locking a vertebral plate is described with respect to FIGS. 10-19. The locking system described in this embodiment is intended for use with any one of a variety of plate systems and configurations including, but not limited to, the specific plates and systems described herein. Referring to FIG. 10, a vertebral plate (203) includes at least one hole (204) having a conical section (205) and a hemispherical section (206). A tapered lock ring (208) has a cut (210) so that it forms a resilient "C" shaped ring. Referring to the cross-sectional view of FIG. 13, the ring (208) has an outside diameter angle $\beta$ and an inside diameter angle $\alpha$. In the preferred embodiment angle $\beta$ is greater than angle $\alpha$, but this may be varied according to desired performance, material properties, and surrounding geometric parameters. Initially, the lock ring (208) is flexed to pass it though the opening (212) of the hole (204) until it re-expands and rests on a shoulder (214) that separates the conical section (205) from the hemispherical section (206), as shown in FIG. 10.

Figure 14:
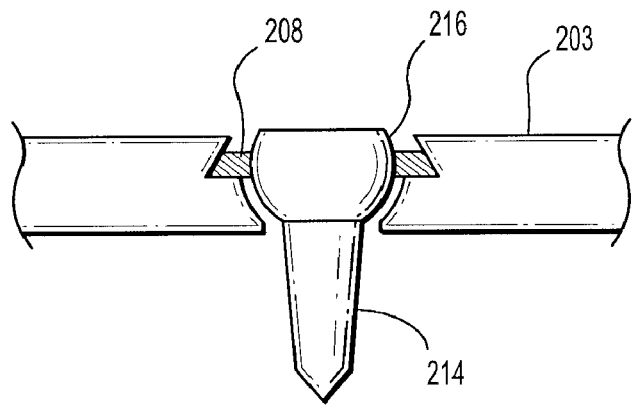
FIG. 14 is a partial, side cross-sectional view of a plate with bone screw and locking ring assembled according to the third embodiment of the present invention.
Figure 15:
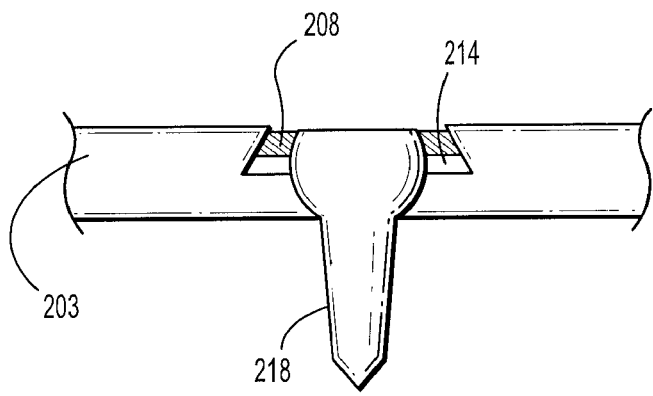
FIG. 15 is a partial, side cross-sectional view of a plate with bone screw and locking ring assembled and locked according to the third embodiment of the present invention.
Figure 16:
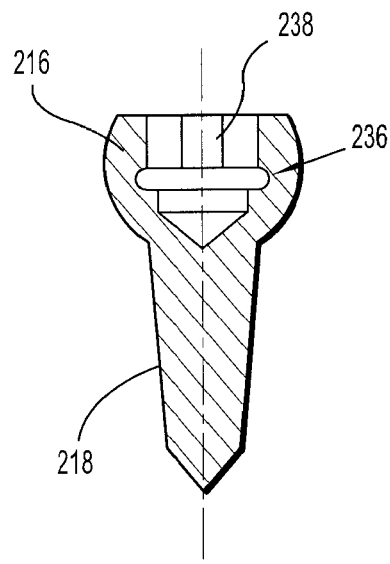
FIG. 16 is a cross-sectional view of a bone screw according to the third embodiment of the present invention.
Figure 17:
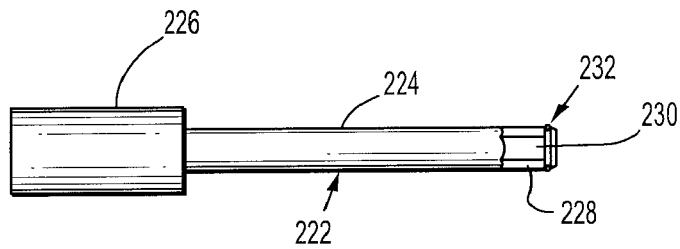
FIG. 17 is a side view of an insertion instrument for use with a bone screw and locking ring according to the third embodiment of the present invention.
Figure 18:
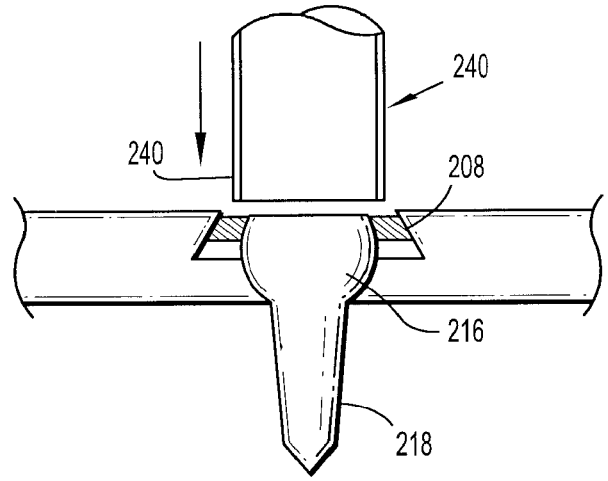
FIG. 18 is a partial side view of the insertion instrument of FIG. 17.

A bone screw (214) having a generally spherical or partially spherical head (216) and a bone-engaging shaft (218) such as a threaded shaft is passed through the hole (204) and ring (208). The maximum diameter section of the screw head (216) is greater than the inner diameter of the lock ring (208) such that, when pushed through the lock ring (208), the screw head (216) expands the ring (208) as shown in FIG. 14. Once the screw head maximum diameter section is past the ring (208), the ring (208) rises upwardly along the contours of the screw head (216) under its own kinetic energy that causes it to return to its original shape, as shown in FIG. 15. In this position, the conical section (205) of the hole (204) mates with the exterior, angled surface (220) of the ring (208).

Torque and rotational movement may be applied to the bone screw (214) by a driver instrument (222). The driver (222) comprises a shaft (224), a handle (226), and a screw-engaging head (228). The head (228) may have flats (230) arid a snap ring (232). The flats (230) cooperate with flats (234) and a ring groove (236) in an opening (238) in the screw head (216). Such torque and rotational movement are applied to the bone screw (214), which is typically threaded, during insertion or removal.

Figure 19:
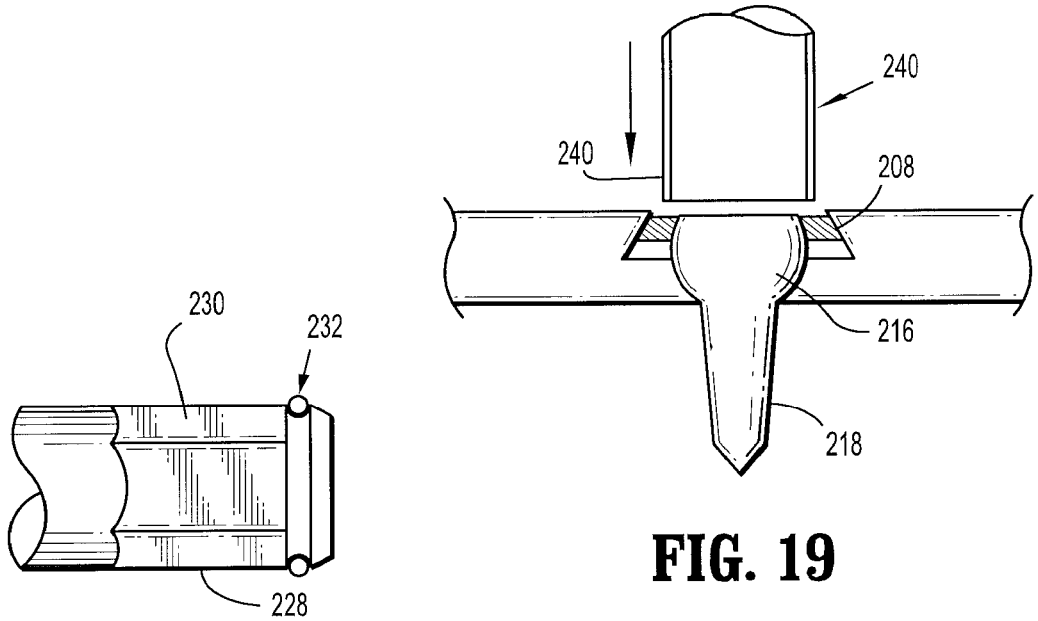
FIG. 19 is a partial side view of the insertion instrument, plate, bone screw and locking ring according, to the third embodiment of the present invention.

During removal, it is necessary to expand and re-position the lock ring (208) downwardly in order to allow passage of the maximum diameter section of the screw head (216) through the lock ring (208). This is achieved by implementing a thin, sleeve end (240) of cylindrical segments in a manner in which it pushes the lock ring (208) downwardly within the hole (204) as shown in FIG. 19. When the ring (208) is pushed downwardly over the screw head (216) it is expanded and held in this position by the sleeve end (204) while the screw (214) is rotated and removed by backing out. After the screw head maximum diameter section is backed out past the ring (208), the ring (208) can be released and the screw (214) removed entirely.

According to another alternative embodiment, the sleeves could be assembled in the plate by chilling the sleeve and heating the plate to cause corresponding respective contraction and expansion, such that when the respective temperatures return to ambient conditions the fasteners, sleeves and plate are relatively locked to each other.

The present invention can be used with or without fusion elements including fusion inserts and fillers such as bone pastes, bone chips and bone morphogenic proteins (BMP). It may also be used by itself or in combination with other devices and it may be used in the cervical spinal applications or other types including lumbar.

Another embodiment of the present invention has various application in which a first structure retains a fastener before, during and after being joined to a second structure by the fastener. While the preferred embodiment is directed to a bone screw for joining a cervical plate vertebral bone, the embodiment is by way of example and is not intended to limit the scope of the invention.

Figure 20:
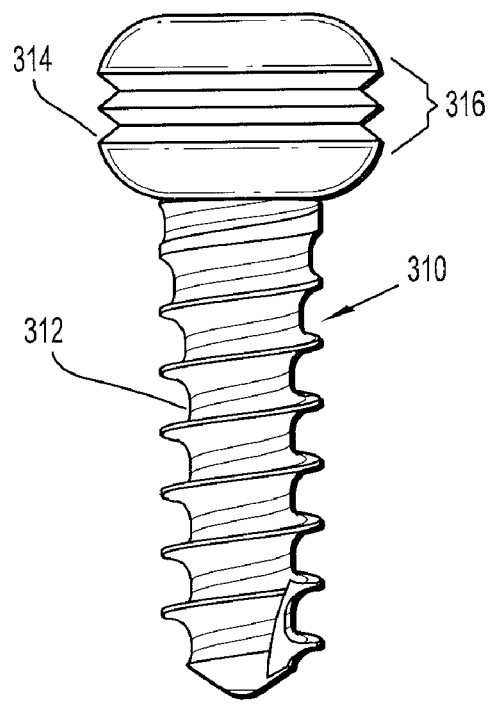
FIG. 20 is a front view of a screw according to the present invention assembly.

As shown in FIG. 20, a bone screw (310) has a shaft portion (312) which can be threaded, a generally spherical head section (314), and a threaded section (316) of helical threads spanning the maximum horizontal diameter. A conventional driver engagement configuration (not shown) on the top of the head (314) such as a slot, a hexagonal hole, or the like is provided to enable rotational force to be applied to the screw (310) for rotationally driving the screw (310). The screw (310) may be made of titanium, stainless steel, or other suitable materials. The head (314) may be a fill sphere, a part-sphere, or a similar configuration in which a maximum horizontal diameter occurs between upper and lower axial sections of the head.

Figure 21:
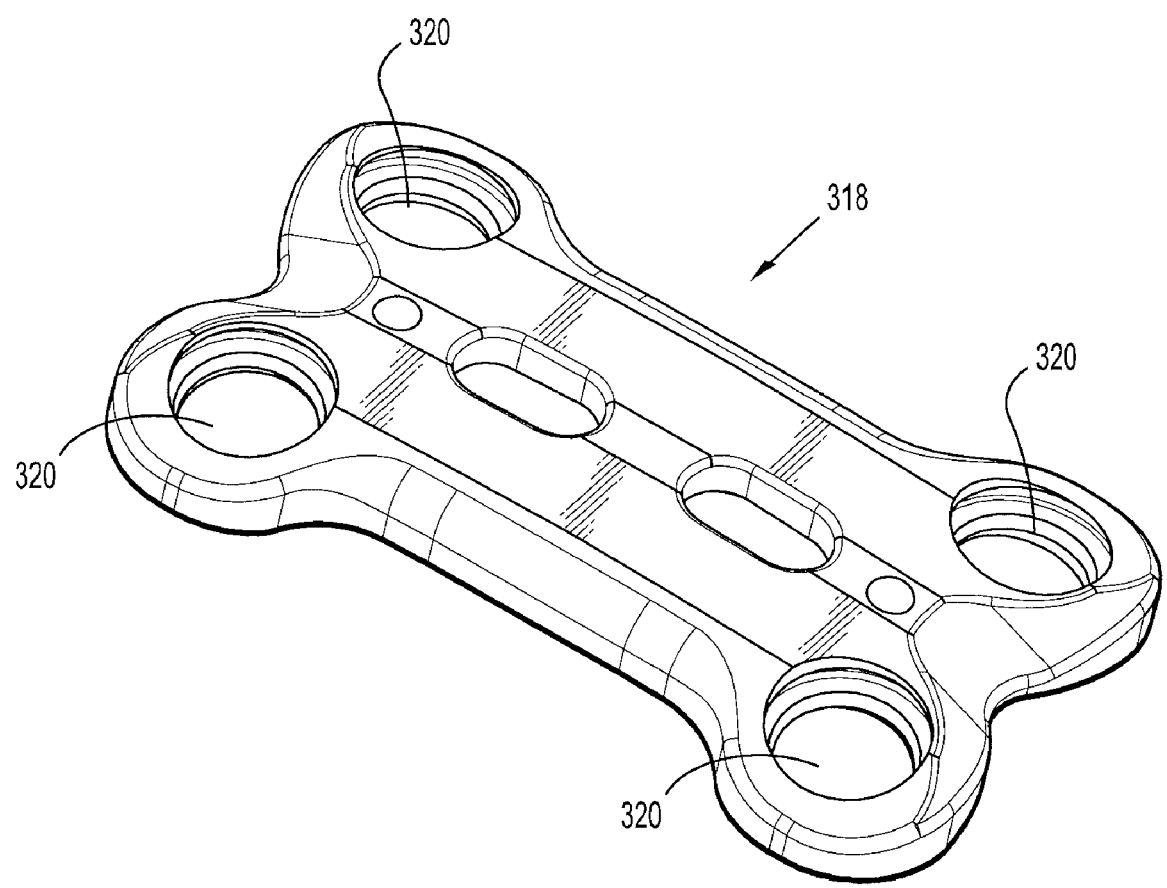
FIG. 21 is a perspective view of a bone plate according to the present invention assembly.
Figure 23:
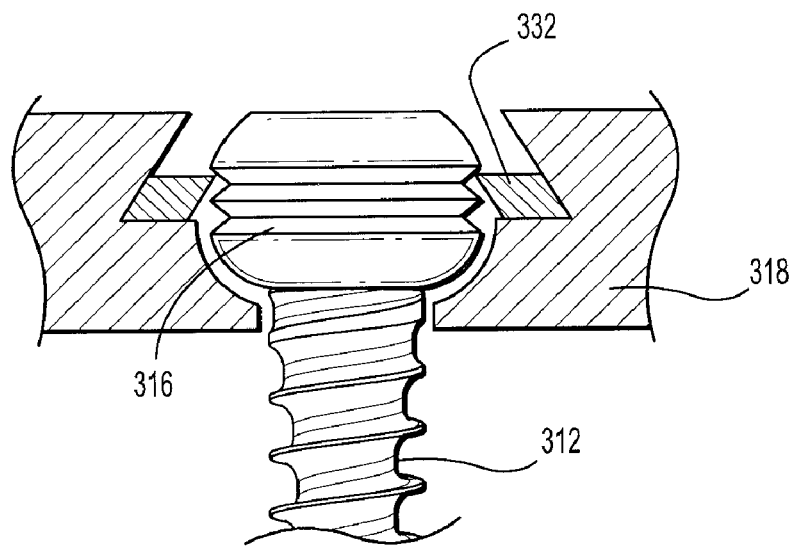
FIG. 23 is a side, cross-sectional view of a retention ring and a partial view of the plate according to the present invention, in which the screw of FIG. 20 is partially advance through the ring.

Referring to FIG. 21, a cervical plate (318) of the type generally known for joining two adjacent vertebra in a stabilizing manner is provided with a plurality of screw holes (320), each adapted to receive the ring component (332) and screw (310) assembly according to the present invention.

Figure 22:
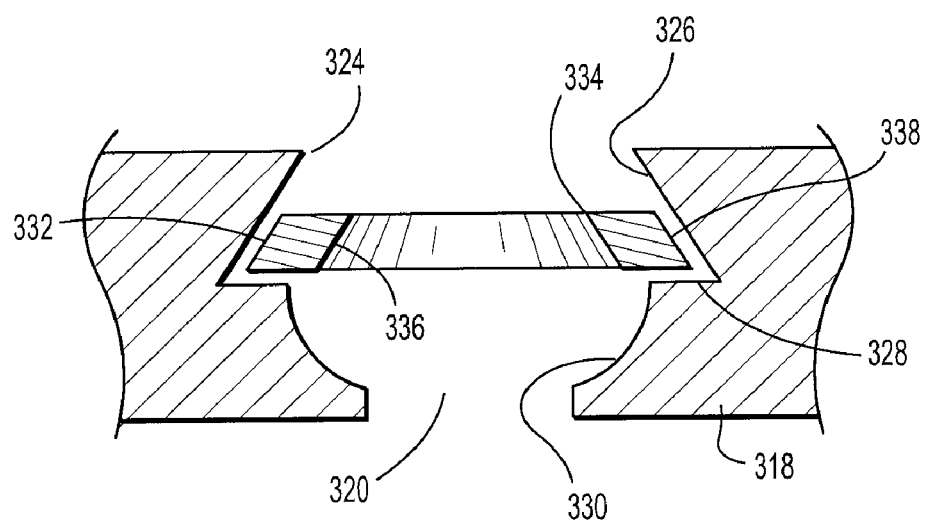
FIG. 22 is a side, cross-sectional view of a retention ring and a partial view of the plate according to the present invention.

As shown in FIG. 22, each hole (320) in the plate (318) has an upper minimum diameter section (324), a tapered section (326) that tapers outwardly in a generally increasing diameter manner downwardly from the upper minimum diameter section (324), a shoulder (328), and a generally tapered seat section (330). A retention ring (332), also shown in top view in FIG. 25, has an inner diameter edge (334), an inner diameter upwardly tapering wall (336), an outer diameter upwardly tapering wall (338), and a slot (340). The retention ring (332) is made from a resilient material that allows it to be stressed or compressed in a manner that allows it to be pressed past the minimum diameter section (324) and into the hole (320) until it sits on the shoulder (328). While seated on the shoulder (328), the ring (332) has expanded back to its unstressed shape since the inner diameter of the tapered section (326) near the shoulder (328) is greater than the outside diameter of the ring (332).

Figure 24:
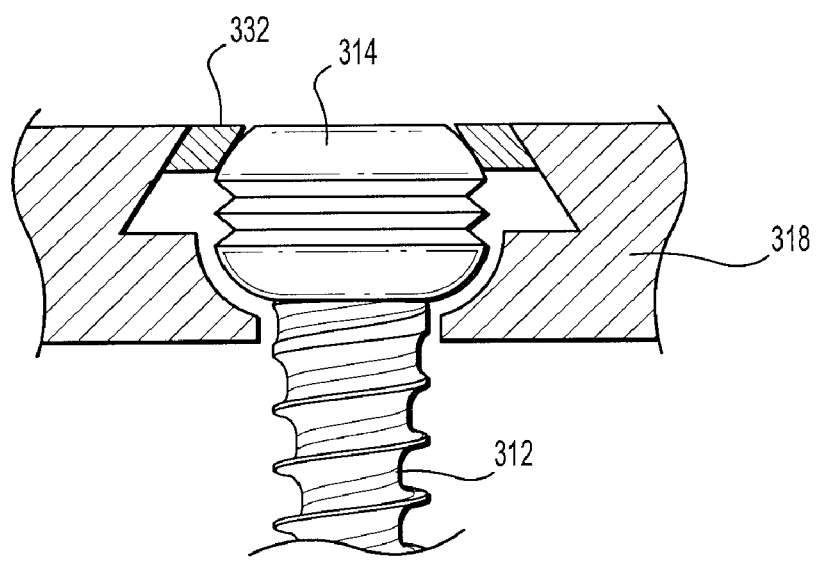
FIG. 24 is a side, cross-sectional view of a retention ring and a partial view of the plate according to the present invention, in which the screw of FIG. 20 is fully advanced through the ring.
Figure 25:
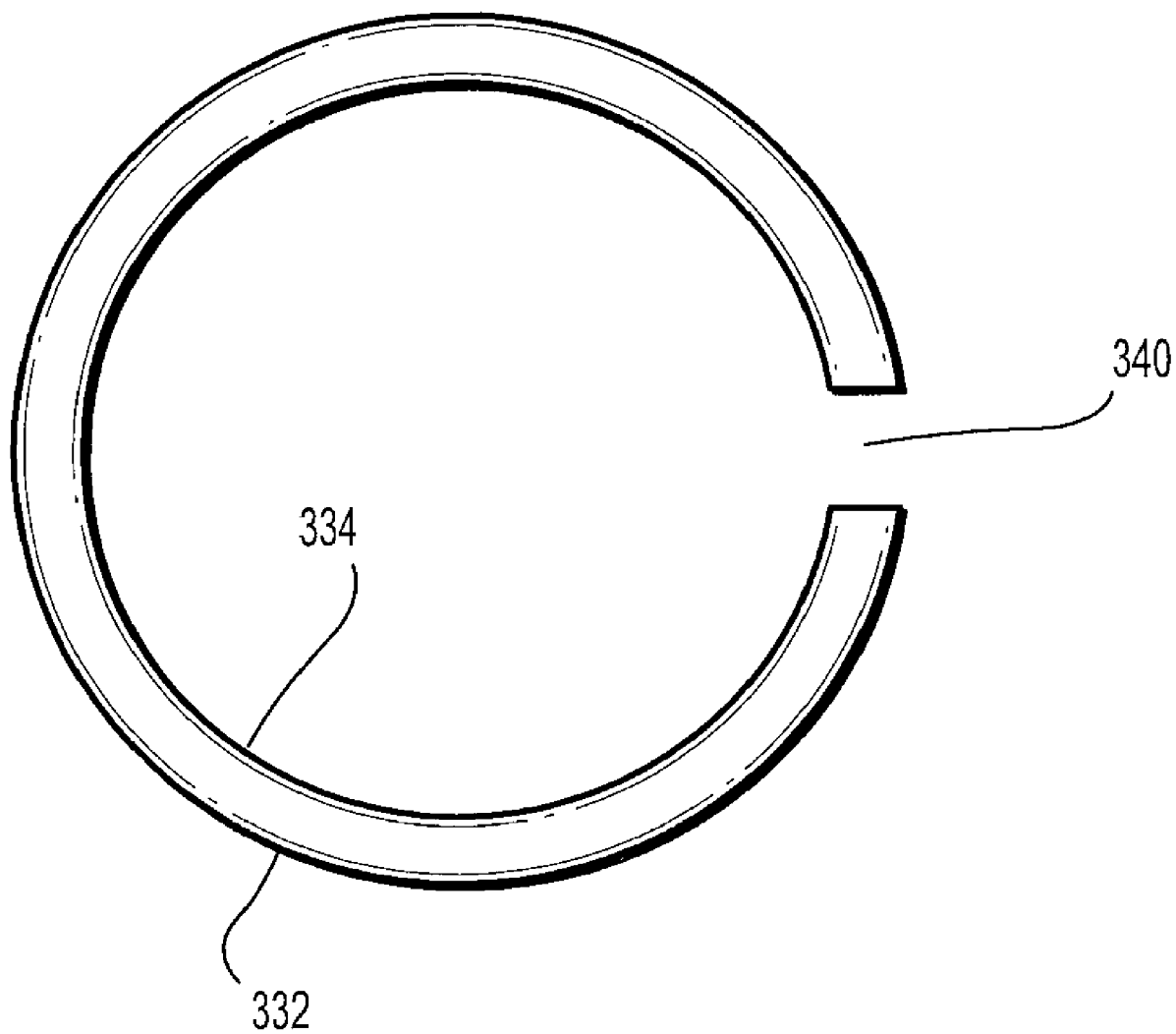
FIG. 25 is a top view of the ring component according to the-present invention.

The screw (310) is placed through the ring (332) and hole (320) and advanced, for example into a vertebral bone, until the head (314) engages the ring (332). As the maximum horizontal diameter of the head (314) moves toward the edge (334) the ring (332) slightly expands until the edge (334) enters the threads (316), as shown in FIG. 24. At this point, the screw (310) is axially advanced further by rotation so the threads (316) ride along the edge (334). As the edge (334) moves past the threaded section (316), it engages the smooth, spherical head of the screw (310) above the threads (316), as shown in FIG. 25.

The ring (310) preferably has a tapered inside wall (336) and a tapered outside wall (338). The hole (320) preferably has a tapered section (326). This combination enables the ring (310) to be wedged between the screw (310) and the plate (318) by the upward force of the screw head (310) which imparts both vertical and horizontal forces to the ring's inner wall (336) which, in turn, are transmitted to the hole's inner wall (326) via the outer wall (338). If upward force of the screw (310) is increased, the ring (310) is wedged tighter. Because the ring cannot be substantially compressed, and because it is appropriately sized with respect to minimum diameter (324), it is prevents the screw head (314) from backing out. The screw head (314) is supported and prevented from slipping out of the hole (320) on the bottom side by a seat (330). The seat (330) may be tapered, conical of hemi-spherical.

In order to release the screw (310) and allow it to be removed from the ring (332) and through-hole (320), a narrow instrument (not shown) must be inserted to push downwardly on the ring (332), causing it to expand slightly around the screw head (314) until the inside edge (334) engages the screw thread (314), at which time counter-rotation will advance the screw head (314) through and out of the ring (332) and through-hole (320) in a manner opposite of its insertion.

While the present invention has been described herein, various modification may be made without departing from the scope of the invention.

What is claimed is:

1. An orthopedic implant assembly, comprising:
a screw retention member, having a bore formed therethrough, the bore having top and bottom ends connected by a passageway having a first diameter at the top end and a second diameter at the bottom end, a tapered retention seat being formed along an intermediate portion of the passageway, the tapered retention seat comprising a shoulder formed at a bottom thereof and a wall that monotonically decreases in diameter over a height thereof;
a frustoconical split ring, having inside and outside diameters that each decrease monotonically over a height thereof from a maximum diameter at a bottom, the split nature of the ring allowing expansion of the inside and outside diameters from a relaxed state; and
a bone screw, comprising a shaft with a head at an end thereof, the head being generally spherical, with a bottom spherical portion, connected to the shaft, and a top spherical portion, the bottom and top spherical portions separated by a threaded section;
wherein the split ring is removably seated in the retention seat and rotating engagement of the threaded section of the bone screw with the top inside diameter of the split ring lifts the split ring in the retention seat from a position below the bone screw head to a position above the bone screw head.

2. The orthopedic implant of claim 1, wherein:
the shaft of the bone screw is threaded from a second end thereof along a sufficient portion thereof to allow effective purchase of bone.

3. The orthopedic implant of claim 1, wherein:
the screw retention member is integrally formed in a surgical implant.

4. The orthopedic implant of claim 1, wherein:
the screw retention member is a sleeve, adapted for fixation to a surgical implant.

5. The orthopedic implant of claim 1, wherein:
the retention seat is tapered frustoconically.

6. A method for fastening an orthopedic implant to a bone, comprising the steps of:
providing the orthopedic implant, the implant having a screw retention member formed within or secured thereto, the screw retention member having a bore therethrough, with a top and a bottom end of the bore connected by a passageway, the bore having a first diameter at the top end and a second diameter at the bottom end, an intermediate portion of the passageway having a tapered retention seat being formed therealong, the tapered retention seat comprising a shoulder formed at a bottom thereof and a wall that monotonically decreases in diameter over a height thereof, with a frustoconical split ring seated in the retention seat, the split ring having inside and outside diameters that each decrease monotonically a height thereof from a maximum diameter at a bottom, the split nature of the ring allowing expansion of the inside and outside diameters from a relaxed state to an expanded state and allowing compression of the inside and outside diameters from the relaxed state to a compressed state;

providing a bone screw, comprising a shaft with a head at a first end thereof, the head being generally spherical, with a bottom spherical portion, connected to the shaft, and a top spherical portion, the bottom and top spherical portions separated by a threaded section; a second end of the shaft adapted for threading purchase of bone;

placing the implant with a bottom surface thereof on the bone, with the bore aligned with a desired point of entry into the bone;

inserting the bone screw rotatingly into the bore, such that the shaft passes through the split ring and the second end of the screw begins to purchase the bone;

continuing to rotatingly insert the bone screw, such that the increasing diameter of the bottom spherical section of the head engages a top edge of the split ring and expands the split ring from the relaxed state into an expanded state, while maintaining and increasing bone purchase;

continuing to rotatingly insert the bone screw, such that the threaded section of the screw head engages the top edge of the expanded split ring and moves the top edge through the threaded section, again maintaining and increasing bone purchase; and continuing to rotatingly insert the bone screw, such that the top edge of the split ring disengages the threaded section, and instead engages the top spherical portion, which then moves into engagement with a tapered inside wall of the split ring, wedging the split ring between the tapered retention seat wall and the top spherical portion, the taper of the retention seat acting to compress the split ring, preventing screw back out.

* * * * *